United States Patent
Ogawa (10) Patent No.: US 8,155,410 B2
(45) Date of Patent: Apr. 10, 2012

(54) IMAGE PROCESSING DEVICE, IMAGE PROCESSING METHOD AND PROGRAM STORAGE MEDIUM

(75) Inventor: Masaharu Ogawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 947 days.

(21) Appl. No.: 12/149,472

(22) Filed: May 2, 2008

(65) Prior Publication Data

US 2008/0285836 A1   Nov. 20, 2008

(30) Foreign Application Priority Data

May 15, 2007 (JP) ................. 2007-129232

(51) Int. Cl.
*G06K 9/00* (2006.01)
(52) U.S. Cl. ...................................... 382/128
(58) Field of Classification Search ........................ None
See application file for complete search history.

(56) References Cited

FOREIGN PATENT DOCUMENTS
JP    2002-204793 A    7/2002
JP    A 2006-304213    11/2006

*Primary Examiner* — Roberto Velez
(74) *Attorney, Agent, or Firm* — Sheldon J. Moss; Chad M. Herring (57) ABSTRACT

An image processing device is provided that corrects image data obtained by sequentially reading out as a current, charges from unit regions from a radiographic image detector provided with signal lines extending along a predetermined direction. The correction includes estimating the respective leakage current superimposed on the read-out current when the charge is read out from a target unit region using a leakage current estimation equation, formed from a single exponential function or from a sum of plural exponential functions, for respective leakage currents of unit regions that are positioned along the same signal line as that of the target unit region and whose charges are in an unread state when the charge is being read out from the target unit region, and correcting the image data corresponding to the target unit region on the basis of the leakage current estimate result.

9 Claims, 8 Drawing Sheets

EXAMPLE OF LEAKAGE CURRENT I REPRESENTED BY A SUM OF AN EXPONENTIAL FUNCTION CORRESPONDING TO A FAST ATTENUATING COMPONENT OF LEAKAGE CURRENT I AND AN EXPONENTIAL FUNCTION CORRESPONDING TO A SLOW ATTENUATING COMPONENT THEREOF

IMAGE PROCESSING DEVICE, IMAGE PROCESSING METHOD AND PROGRAM STORAGE MEDIUM

CROSS-REFERENCE TO RELATED APPLICATION

This application claims priority under 35 USC 119 from Japanese Patent Application No. 2007-129232, the disclosure of which is incorporated by reference herein.

BACKGROUND OF THE INVENTION

1. Field of the Invention

The invention relates to an image processing device, an image processing method, and an image processing program storage medium, and particularly relates to: an image processing device in which correction is performed to an image obtained by reading out, as a current, charge from a radiographic image detector in which the charge which is formed by converting irradiated radiation is accumulated and stored; to an image processing method applicable to the image processing device; and to a storage medium storing an image processing program to cause a computer to function as the image processing device.

2. Description of the Related Art

Systems that obtain digital radiographs are known in radiography for medical diagnostic purposes. In these systems, radiation passing through the image target is irradiated onto a radiographic image detector provided with a photoelectric conversion layer sensitive to radiation, charges that are accumulated in the radiographic image detector according to the amount of radiation irradiated on the radiographic image detector are sequentially read out as current for each unit region for reading out, and the read-out current is converted into digital data. In such a radiographic image detector, when charge is read out from a given unit region, leakage current may occur from the unit regions with charge that is yet to be read out, with this leakage current being superimposed on the current being read out and leading to a deterioration in the image quality of the read-out image.

To address this issue, Japanese Patent Application Laid-Open (JP-A) No. 2006-304213 discloses a technique for obtaining an image with the influence of leakage current removed therefrom. In this technique, unit regions with condensers for accumulating charge converted in an X-ray conversion layer, and with thin film transistors (TFTs), for reading out the charge accumulated in the condensers by switching of on/off, are two-dimensionally arrayed, and plural gate lines and plural signal lines are also two-dimensionally arrayed. In such a configuration, after charge has been read out from all of the unit regions, a value as the leakage current when reading out the charge of a particular unit region, is derived by summing up all of the signal levels for each unit region that is connected to the same data line as the particular unit region and whose charge is unread when the particular unit region is read out, and multiplying coefficient A by the summed value. The signal level of the particular unit region is corrected according to the derived leakage current values, and an image removed of the influence of leakage current is obtained by carrying out such correction to all of the unit regions.

However, it is found apparent from the investigations carried out by the inventor of the present application that the leakage current from individual regions in the radiographic image detector attenuate with time (details of these investigations are given below). However, the above technology does not consider the above changes in the leakage current due to attenuation with time, and the precision of correction for leakage current influence is insufficient.

SUMMARY OF THE INVENTION

The invention is made in consideration of the above circumstances, and provides an image processing device enabling precise correction of the influence of leakage current superimposed on read-out charge from a radiographic image detector, and an image processing method and storage medium storing an image processing program of the same.

A first aspect of the invention is an image processing device processing image data obtained from a radiographic image detector that is provided with signal lines extending along a predetermined direction, converts irradiated radiation into charge, and accumulates and holds the converted charge, the image data being obtained by sequentially reading out, as a current through the signal lines, the charge from each of unit regions to be read out from the radiographic image detector, the device including:

a correction section that corrects the image data for each unit region, the correction section estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, . . . ) that are positioned along the predetermined direction on the same signal line as that of the target unit region and whose charges are in an unread state when the charge of the target unit region is being read out, and the correction section correcting the image data corresponding to the target unit region on the basis of the leakage current estimate result;

wherein the exponential function(s) has as a variable one of:

(a) elapsed time from the time of leakage current generation of the unit region j up to when charge is read out therefrom, (b) elapsed time from starting to read out charge of the radiographic image detector up to when charge is read out from the unit region j, or (c) position along the predetermined direction of the target unit region when charge is read out therefrom by scanning the target unit regions to be readout along the predetermined direction.

A second aspect of the invention is an image processing method processing image data obtained from a radiographic image detector being provided with signal lines extending along a predetermined direction, converting irradiated radiation into the charge, and accumulating and holding the converted charge, the image data being obtained by sequentially reading out a charge, as a current through signal lines, from each of unit regions to be read out from the radiographic image detector, the method including:

correcting the image data for each unit region by estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, . . . ) that are positioned along the predetermined direction on the same signal line as that of the target unit region and whose charges are in an unread state when the charge of the target unit region is being read out, and correcting the image data corresponding to the target unit region on the basis of the leakage current estimate result;

wherein the exponential function(s) has as a variable one of:

(a) elapsed time from the time of leakage current generation of the unit region j up to when charge is read out therefrom, (b) elapsed time from starting to read out charge of the radiographic image detector up to when charge is read out from the unit region j, or (c) position along the predetermined direction of the target unit region when charge is read out therefrom by scanning the target unit regions to be readout along the predetermined direction.

A third aspect of the invention is storage medium storing a program for causing a computer to execute image data processing on image data obtained from a radiographic image detector being provided with signal lines extending along a predetermined direction, converting irradiated radiation into the charge, and accumulating and holding the converted charge, the image data being obtained by sequentially reading out a charge, as a current through signal lines, from each of unit regions to be read out from the radiographic image detector, the image data processing including:

correcting the image data for each unit region by estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, . . . ) that are positioned along the predetermined direction on the same signal line as that of the target unit region and whose charges are in an unread state when the charge of the target unit region is being read out; and correcting the image data corresponding to the target unit region on the basis of the leakage current estimate result;

wherein the exponential function(s) has as a variable one of:

(a) elapsed time from the time of leakage current generation of the unit region j up to when charge is read out therefrom, (b) elapsed time from starting to read out charge of the radiographic image detector up to when charge is read out from the unit region j, or (c) position along the predetermined direction of the target unit region when charge is read out therefrom by scanning the target unit regions to be readout along the predetermined direction.

The image processing program provides a computer with the functionality of the above correction method. Accordingly, by executing the image processing program, the computer may function as the image processing device of the first aspect.

BRIEF DESCRIPTION OF THE DRAWINGS

An exemplary embodiment of the present invention will be described in detail based on the following figures, wherein.

DETAILED DESCRIPTION OF THE INVENTION

Figure 1:
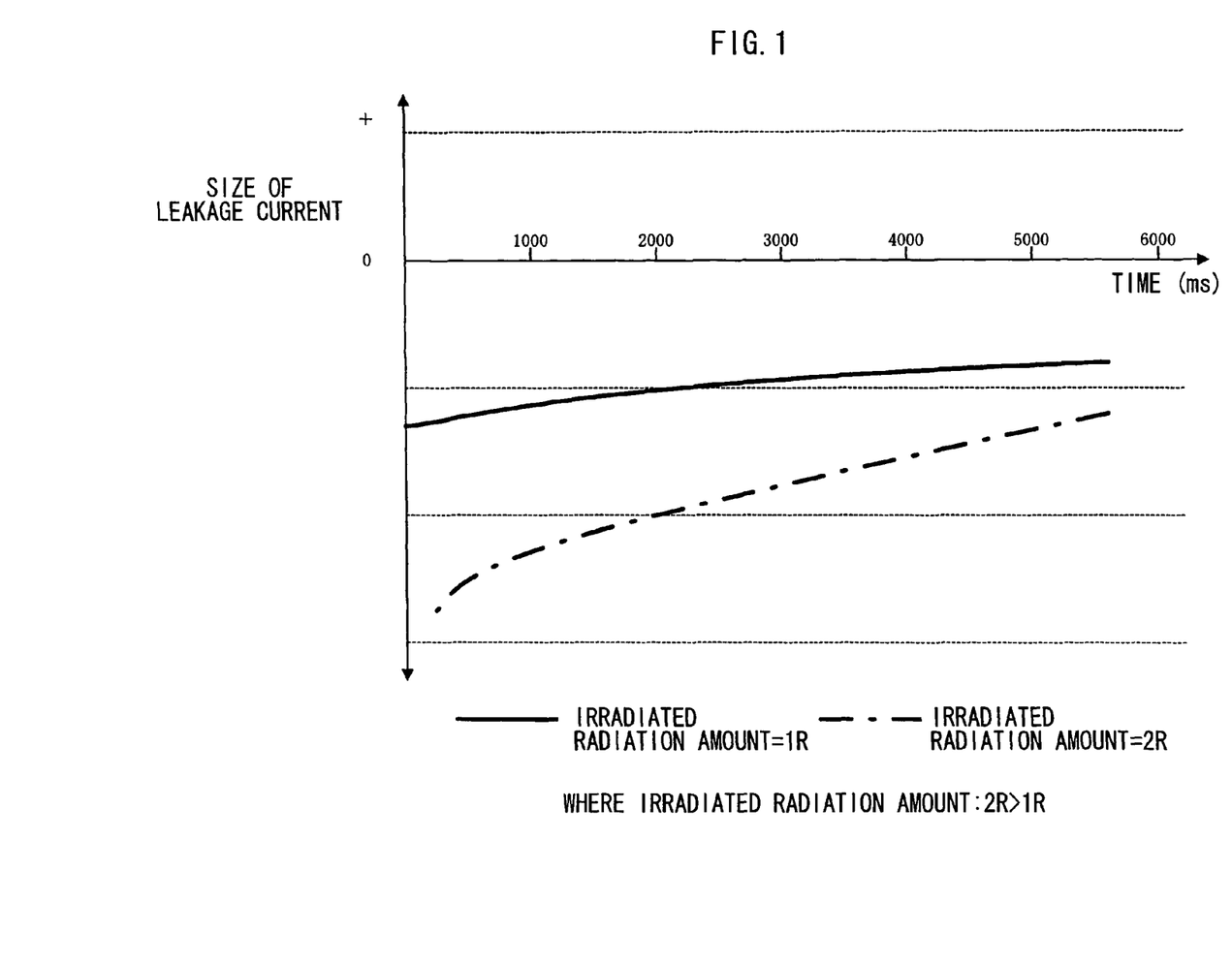
FIG. 1 is a graph showing results of an experiment carried out by the current inventor.

The inventor has undertaken investigations into the characteristics of leakage current superimposed on the read-out current when an image is read out from a radiographic image detector (i.e., when charges accumulated/held in an radiographic image detector according to the irradiated radiation amount, are successively read out from each unit region as a current). These investigations use a radiographic image detector (optical reading type radiographic image detector) configured so that when light is irradiated thereon, the charge held in each unit region corresponding to the location that the light is irradiated is output as a current. In these investigations, after a particular amount of radiation has been irradiated on the radiographic image detector, the charge flowing in signal lines extending in a predetermined direction in the radiographic image detector is measured over a set duration of time in a state in which the reading light for reading out the image (charge) is not being irradiated, and these measurements are carried out for various different amounts of irradiated radiation. The results of these investigations are shown in FIG. 1.

In these investigations, the current flowing in the signal lines is supposed to be zero, since there is no reading light irradiated to the optical reading-type radiographic image detector. However, as is apparent from FIG. 1, the investigations have observed that in reality there is a leakage current, dependent on the irradiated radiation amount, flowing in the signal lines, and also that the size of the leakage current gradually reduces with the passage of time (while not shown in abbreviated FIG. 1, the size of the leakage current approaches, and ultimately becomes zero). In FIG. 1, a leakage current in the direction of the read-out current is shown with a "+" sign, and a leakage current in the opposite direction thereto is shown with a "−" sign. The leakage current may be considered to be the total sum of leakage currents from each of the unit regions on the signal line corresponding to the signal line that the current measurement is performed.

The inventor has discovered that the pattern of change of current obtained in such investigations shows a steep current change gradient when the difference in the current from the supposed current value (i.e. from zero) is large, and shows a shallow current change gradient when the difference in the current from the supposed current value is small. Namely, the change pattern shown is one that is proportional to the difference from the supposed current value. Accordingly it has been found from the above that it is possible to approximate (estimate) with good precision the size of the current superimposed on the read-out current with a single exponential function (in particular an exponential function exp X with the natural log e (Napier's constant) as the base thereof), or as the sum of plural exponential functions (in particular exponential functions exp X), with the elapsed time from the time of leakage current generation (for example, in an optical reading-type radiographic image detector, the time of cessation of application of high voltage to the radiographic image detector) as a variable thereof. By finding that it is possible to approximate (estimate) with good precision the size of the total leakage current (superposition) for each unit region with a single exponential function (in particular an exponential function exp X), or as the sum of plural exponential functions (in particular exponential functions exp X), the inventor has found that the leakage current for individual unit regions may also be approximated (estimated) with good precision with a single exponential function (in particular an exponential function exp X), or as the sum of plural exponential functions (in particular exponential functions exp X).

Moreover, the duration from the time of leakage current generation up to starting to read out the image (charge) from the radiographic image detector is often constant. The inventor has accordingly also found that it is possible to substitute the above exponential function with an exponential function using the elapsed time from starting to read out the charge from the radiographic image detector as a variable. Furthermore, when charge is read out by scanning the target unit regions that the charge thereof is to be read-out along the predetermined direction, the position along the predetermined direction of the target unit region approximately corresponds to the elapsed time from starting of reading-out of the charge from the radiographic image detector. Therefore, the inventor has found that it is possible to substitute the above exponential function with an exponential function using the position of the target unit region along the predetermined direction as a variable. The inventor has also found that: charge held by individual unit regions, leaking out as a current, is a cause of the above leakage current; unit regions of the radiographic image detector which have completed charge read-out do not generate leakage current since they hold no charge; leakage current from unit regions that are in an unread state is output through the corresponding signal line; and aforementioned findings also apply to a radiographic image detector other than optical reading-type radiographic image detectors (such as, for example, TFT-type radiographic image detectors) since the electrical resistance for holding charge in individual unit regions is not infinite.

Figure 2:
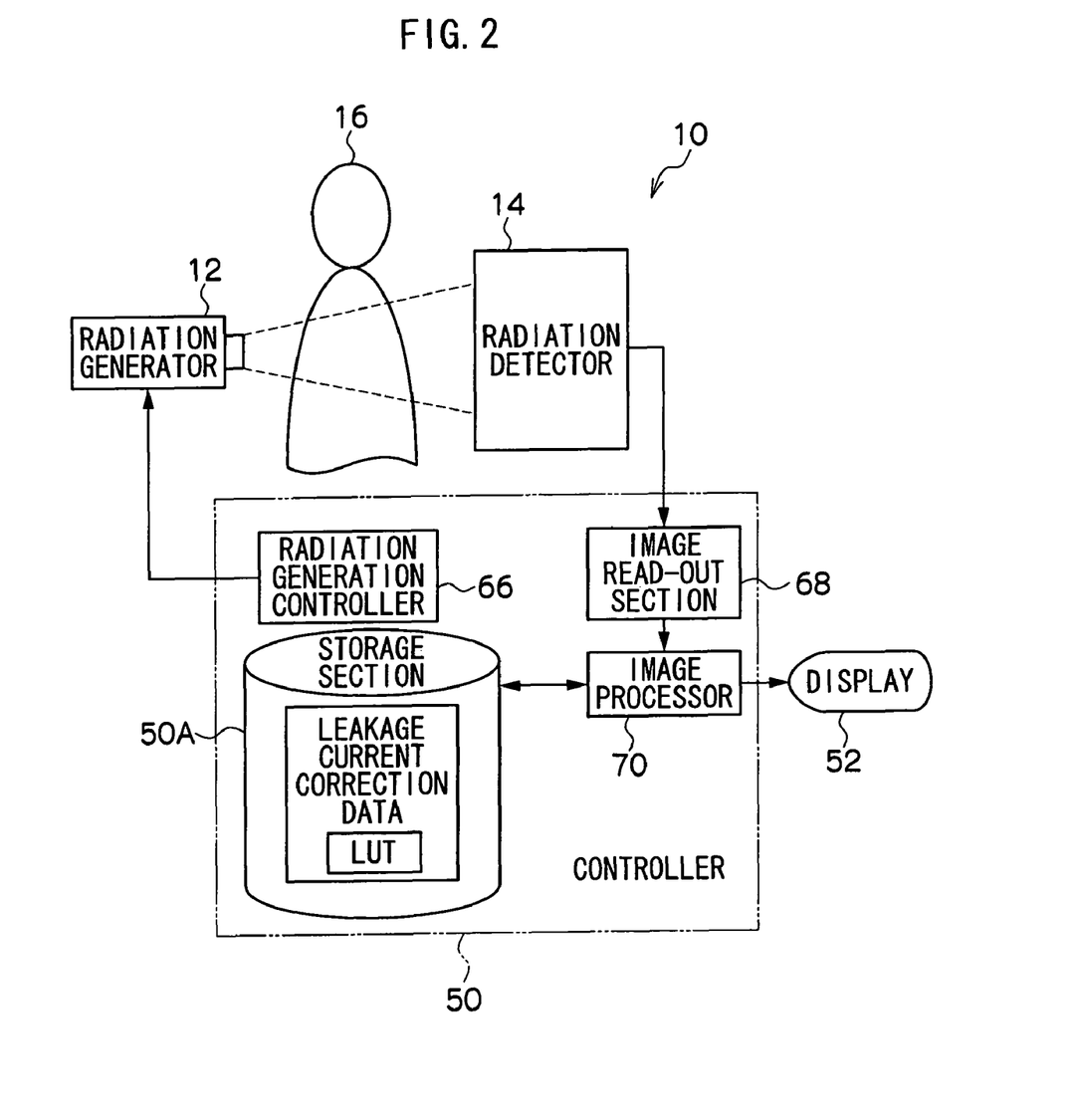
FIG. 2 is a block diagram showing a schematic configuration of a radiographic image photographing device according to the exemplary embodiment.

Based on the above conception, an exemplary embodiment of the present invention will be described in detail hereinafter with reference to the drawings. A radiographic image photographing device 10 relating to the exemplary embodiment is shown in FIG. 2. The radiographic image photographing device 10 includes a radiation generator 12 which generates radiation such as X-rays, and a radiation detector 14 which is provided so as to be spaced apart from the radiation generator 12. The region between the radiation generator 12 and the radiation detector 14 is a photographing position at which a subject 16 is positioned at the time of photographing. The radiation, which exits from the radiation generator 12 and carries image information by passing through the subject 16 positioned at the photographing position, is irradiated onto the radiation detector 14.

The radiation detector 14 is structured to include a radiographic image detector. The radiographic image detector includes an electrostatic recording portion which includes a photoconductive layer which exhibits electrical conductivity by receiving the irradiation of the radiation. The radiographic image detector receives the irradiation of radiation carrying image information, and records the image information in the electrostatic recording portion, and outputs image signals expressing the recorded image information. Examples of the radiographic image detector are an optical-reading-type radiographic image detector which reads the image information recorded in the electrostatic recording portion by using a semiconductive material which generates charges due to the irradiation of light, and a TFT-type radiographic image detector which accumulates charges generated due to the irradiation of radiation and reads the accumulated charges by turning switching elements, such as thin film transistors (TFTs), on/off per pixel, and the like. Hereinafter, the structure of an optical-reading-type radiographic image detector 20 will be described as an example.

Figure 3A:
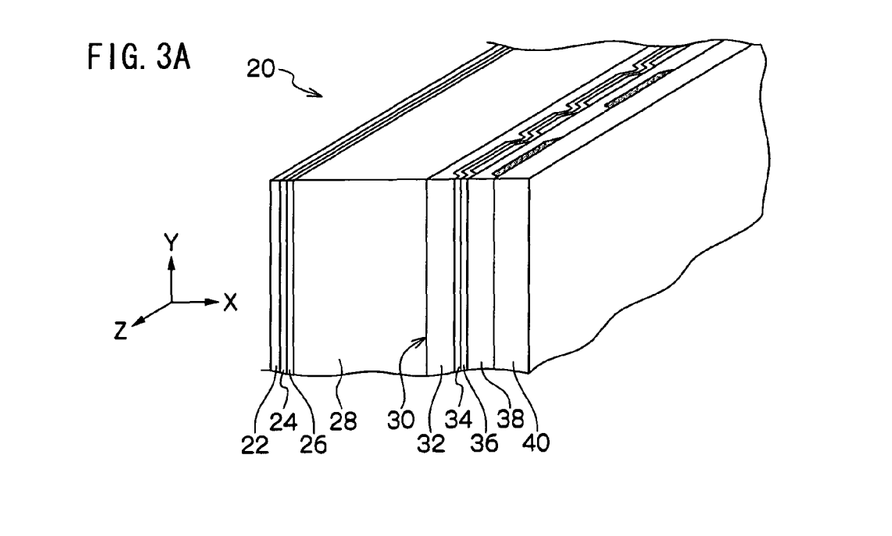
FIG. 3A is a perspective view of a radiographic image detector.
Figure 3B:
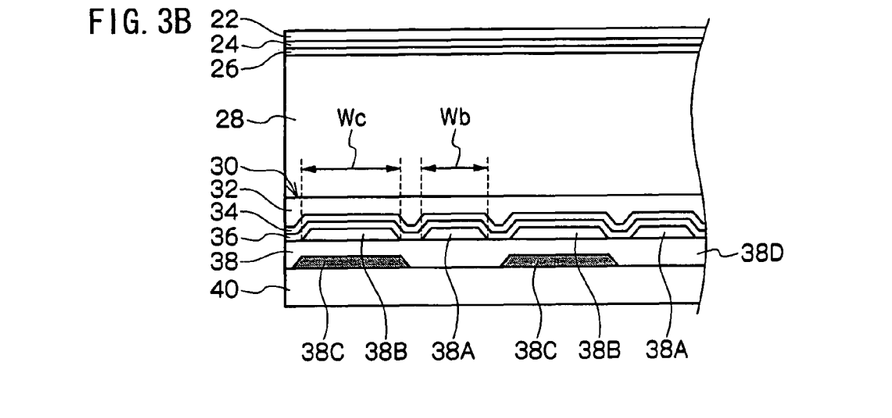
FIG. 3B is a cross-section taken along plane X-Z of FIG. 3A.
Figure 3C:
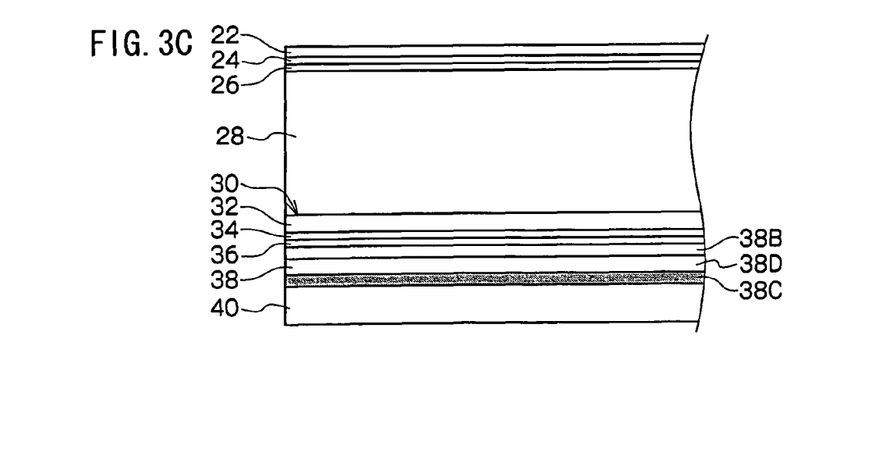
FIG. 3C is a cross-section taken along plane X-Y of FIG. 3A.
Figure 4:
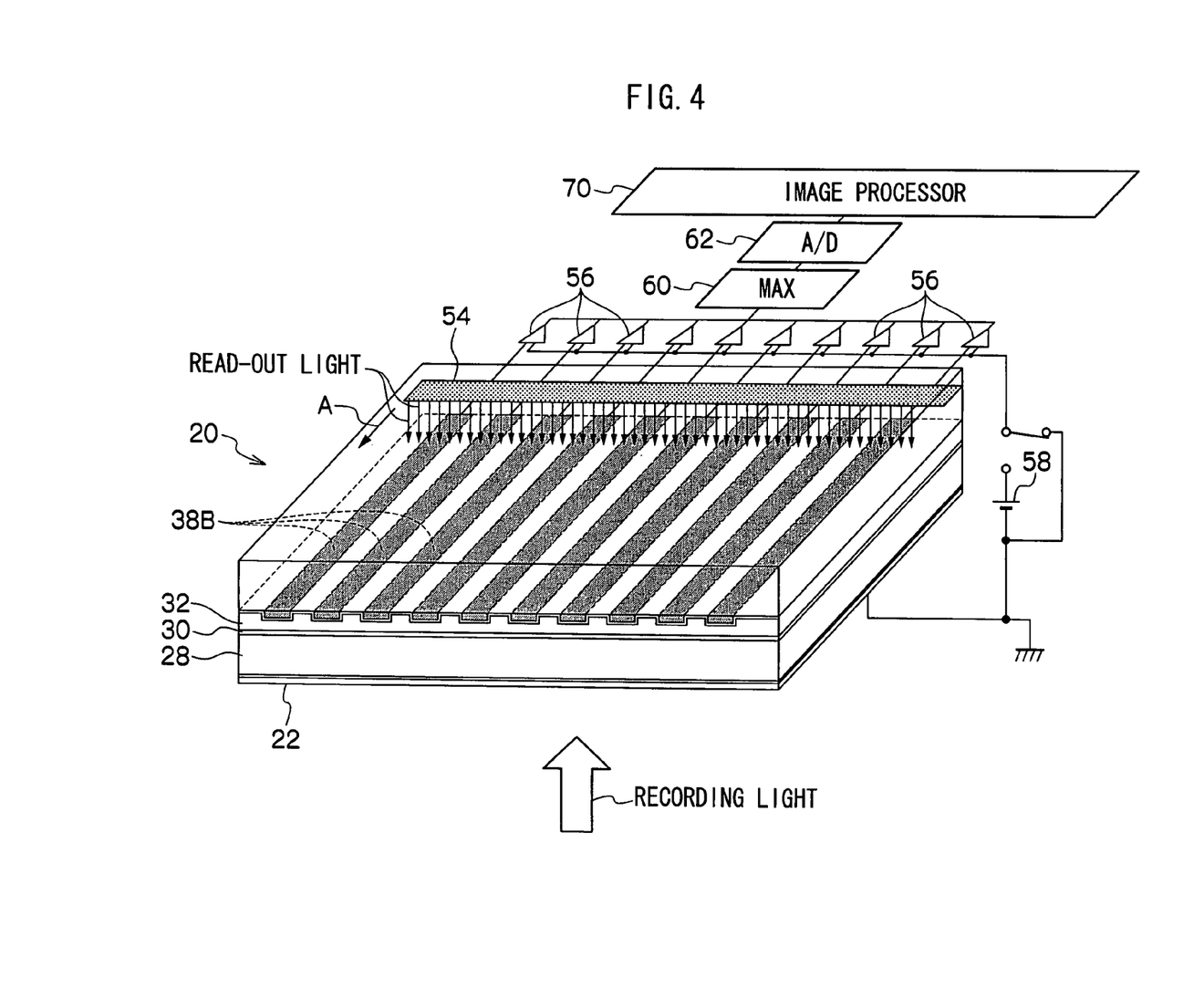
FIG. 4 is a schematic diagram of a radiographic image detector including electrodes and an image read-out section.

As shown in FIG. 3A through FIG. 3C, the optical-reading-type radiographic image detector 20 is structured by a first electrode layer 22, a photoconductive layer for recording (recording photoconductive layer) 28, a photoconductive layer for reading (reading photoconductive layer) 32, a second electrode layer 38, and a substrate 40 being provided in that order. The first electrode layer 22 is transmissive with respect to the radiation from the radiation generator 12 (which is called "recording light" in order to distinguish it from "reading light" which will be described later). The recording photoconductive layer 28 generates charge pairs and exhibits electrical conductivity when the recording light, which is transmitted through the first electrode layer 22, is irradiated thereon. The reading photoconductive layer 32 generates charge pairs and exhibits electrical conductivity when reading light is irradiated thereon. The second electrode layer 38 is formed from first transparent linear electrodes 38A, second transparent linear electrodes 38B, light blocking films 38C and an insulating layer 38D. The substrate 40 is transmissive with respect to reading light. Note that the second transparent linear electrodes 38B corresponds to the signal line of the present invention. Further, as shown in FIG. 4, a linear light source 54, which is for irradiating reading light onto the radiographic image detector 20, is provided at the substrate 40 side of the radiographic image detector 20.

An electron injection impeding layer 24, which suppresses electron injection from the first electrode layer 22, and a crystallization preventing layer 26, which suppresses crystallization of the recording photoconductive layer 28, are provided in that order between the first electrode layer 22 and the recording photoconductive layer 28. A crystallization preventing layer 34, which suppresses crystallization of the reading photoconductive layer 32, and a hole injection impeding layer 36, which suppresses hole injection from the transparent linear electrodes 38A, 38B when high voltage is applied, are provided in that order between the reading photoconductive layer 32 and the second electrode layer 38. Further, a charge accumulating section 30, which accumulates latent image polarity charges (i.e., charges forming a latent image), and which carry the radiographic image generated within the recording photoconductive layer 28, is formed two-dimensionally at the interface between the recording photoconductive layer 28 and the reading photoconductive layer 32.

The size (surface area) of the radiographic image detector 20 can be made to be, for example, greater than or equal to 20 cm×20 cm, and in particular, about an effective size of 43 cm×43 cm in the case of photographing the chest. Further, the hole injection impeding layer 36 can be structured of $CeO_2$, ZnS, or the like which are exemplary materials. The layer may be a single layer, or may be laminated in many layers in order to strengthen the positive hole impeding ability (and in order to reduce dark current). The thickness of the hole injection impeding layer 36 may be greater than or equal to 20 nm and less than or equal to 100 nm. The electron injection impeding layer 24 can be structured of a material such as $Sb_2S_3$ or an organic compound. The electron injection impeding layer 24 also may be a single layer, or may be laminated in many layers. Further, for the crystallization preventing layers 26, 34, binary systems such as Se—As, Se—Ge, Se—Sb compounds, or ternary systems such as Se—Ge—Sb, Se—Ge—As, Se—Sb—As, which have a high crystallization temperature, may be used.

A photoconductive substance whose main component is a-Se (amorphous selenium) may be used for the recording photoconductive layer 28. The thickness of the recording photoconductive layer 28 may be greater than or equal to 50 μm and less than or equal to 1000 μm, in order to be able to sufficiently absorb the recording light. Moreover, photoconductive substances whose main component is Se, such as, for example, a-Se which is doped with 10 to 200 ppm of Cl which has a large difference between the mobility of negative charges charged at the first electrode layer 22 and the mobility of positive charges which are the opposite polarity thereof, or Se—Ge, Se—Sb, Se—As, and the like may be used for the reading photoconductive layer 32. The thickness of the reading photoconductive layer 32 may be less than or equal to ½ of the thickness of the recording photoconductive layer 28. Moreover, the thinner the reading photoconductive layer 32, the better the responsiveness at the time of reading. Therefore, the thickness of the photoconductive layer for reading 32 may be made to be, for example, less than or equal to 1/10 and further, less than or equal to 1/100 of the thickness of the recording photoconductive layer 28.

The aforementioned materials of the respective layers are examples in cases in which negative charges are charged to the first electrode layer 22, positive charges are charged to the transparent linear electrodes 38A, 38B of the second electrode layer 38, negative charges serving as latent image polarity charges (i.e., charges forming a latent image) are accumulated in the charge accumulating section 30 formed at the interface of the recording photoconductive layer 28 and the reading photoconductive layer 32, and the photoconductive layer for reading 32 is made to function as a so-called positive hole transport layer in which the mobility of the positive charges, which serve as transport polarity charges (i.e., transporting charges), is greater than the mobility of the negative charges serving as the latent image polarity charges which are the opposite polarity of the transporting charges. However, the polarities of these charges may respectively be opposite polarities. When the polarities are reversed in this way, it suffices to perform minor changes such as changing the reading photoconductive layer which functions as a positive hole transport layer into a reading photoconductive layer which functions as an electron transport layer. Further, the reading photoconductive layer 32 may be made to be a layer whose main component is a-Se, and an As2Se3, GeSe, GeSe2, or Sb2Se3 layer may be provided as the charge accumulating section 30.

It suffices for the first electrode layer 22 and the first transparent linear electrodes 38A to be transmissive with respect to recording light or reading light. For example, in a case in which the layer is made to be transmissive with respect to visible light, an oxide metal such as SnO2, ITO (Indium Tin Oxide) or IZO (Indium Zinc Oxide) which are known as light-transmissive metal thin films, or IDIXO (Indium X-metal Oxide manufactured by Idemitsu Kosan Co., Ltd.), which is an amorphous light-transmissive oxide metal which can be easily etched can be made to be a thickness of about 50 to 200 nm, and preferably greater than or equal to 100 nm, and used. Further, when X-rays are used as the recording light and the X-rays are irradiated from the first electrode layer 22 side to record a radiographic image, the first electrode layer 22 does not need to be transmissive with respect to visible light. Therefore, the first electrode layer 22 may be formed by using a pure metal of Al or Au or the like of a thickness of 100 nm, for example.

The first transparent linear electrodes 38A of the second electrode layer 38 are arrayed in the form of stripes at a pitch of unit region (unit region pitch). The unit region pitch can be made to be about 50 to 250 μm in order to realize a high S/N ratio while maintaining high sharpness in X-ray photography for medical care. Within this range of the unit region pitch, the width of the first transparent linear electrode 38A can be made to be about 10 to 200 μm. Further, the second transparent linear electrodes 38B of the second electrode layer 38 are provided as electrically conductive members for outputting electrical signals of levels corresponding to the amounts of the latent image polarity charges accumulated in the charge accumulating section 30. Similarly to the first transparent linear electrodes 38A, the second transparent linear electrodes 38B are arrayed in the form of stripes. By setting the electrodes of the second linear electrode layer 38 in the form of stripes, correction of structure noise can be made to be simple, the S/N ratio of the image can be improved by lowering the capacitance, and parallel reading (mainly in the main scanning direction) can be carried out such that the reading time can be shortened.

At the second electrode layer 38, the second transparent linear electrodes 38B and the first transparent linear electrodes 38A are arrayed so as to be disposed parallel to one another. The aforementioned light-transmissive metal thin films may be used as the second transparent linear electrodes 38B. In this case, patterns of the first transparent linear electrodes 38A and the second transparent linear electrodes 38B can be formed simultaneously in a single lithography process. In this case, the light blocking films 38C, which are formed from members having poor light transmissivity, are provided at the portions on the substrate 40 which correspond to the respective second transparent linear electrodes 38B, such that the irradiation intensity of the reading light onto the second transparent linear electrodes 38B will be smaller than the irradiation intensity of the reading light onto the first transparent linear electrodes 38A. In this way, a transmissivity Pc with respect to the reading light can be made to be less than or equal to 10%, or in other words, a light blocking ability can be provided. Thereby, it is possible for charge pairs for signal take-out to not be generated within the portions of the reading photoconductive layer 32 which correspond to the second transparent linear electrodes 38B. Further, the hole injection impeding layer 36, which is a thin film of less than or equal to 100 nm, is formed on the first transparent linear electrodes 38A and the second transparent linear electrodes 38B. Moreover, predetermined distances are provided between the respective first transparent linear electrodes 38A and the respective second transparent linear electrodes 38B so that they are electrically insulated.

At the radiographic image detector 20, a width Wc of the second transparent linear electrodes 38B may be made wider than a width Wb of the first transparent linear electrodes 38A, and a transmissivity Prb of the first transparent linear electrodes 38A with respect to the reading light and a transmissivity Prc of the second transparent linear electrodes 38B with respect to the reading light may be set to satisfy the conditional formula:

$$(Wb \times Prb)/(Wc \times Prc) \geq 5$$

In this case, together with making the width Wc of the second transparent linear electrodes 38B wider than the width Wb of the first transparent linear electrodes 38A, at the time of recording an electrostatic latent image, the first transparent linear electrodes 38A and the second transparent linear electrodes 38B are connected, and the second transparent linear electrodes 38B are actively utilized in the formation of the electric field distribution. When the first transparent linear electrodes 38A and the second transparent linear electrodes 38B are connected in this way and recording is carried out, the latent image polarity charges are accumulated not only at the positions corresponding to the first transparent linear electrodes 38A, but also at the positions corresponding to the second transparent linear electrodes 38B. When the reading light is irradiated through the first transparent linear electrode 38A to the reading photoconductive layer 32 at the time of reading, the latent image polarity charges of the regions above the two second transparent linear electrodes 38B which sandwich the first transparent linear electrode 38A are successively read-out via the two second transparent linear electrodes 38B. Accordingly, in this case, the position corresponding to the first transparent linear electrode 38A becomes the center of a unit region, and respective halves of the second transparent linear electrodes 38B, which are sandwiching this first transparent linear electrode 38A at the both sides thereof, become one unit region in the direction in which the first transparent linear electrodes 38A and the second transparent linear electrodes 38B are lined-up. Further, electrically conductive members having better electrical conductivity than the first transparent linear electrodes 38A and the second transparent linear electrodes 38B may be used as bus lines, and may be provided for each of the respective first transparent linear electrodes 38A and each of the respective second transparent linear electrodes 38B so as to extend in the lengthwise directions thereof.

The light blocking films 38C do not necessarily have to be a material which is insulating, and materials which are such that the specific resistance of the light blocking films 38C becomes greater than or equal to $2\times10^{-6}$ Ω·cm (and more preferably, less than or equal to $1\times10^{15}$ Ω·cm) can be used. For example, if the material which is used is a metal material, Al, Mo, Cr or the like can be used. If the material which is used is an inorganic material, MoS2, WSi2, TiN, or the like can be used. Note that it is more preferable to use a material such that the specific resistance of the light blocking films 38C becomes greater than or equal to 1 Ω·cm. Further, when an electrically conductive material such as a metal material is used as the light blocking films 38C, in order to avoid direct contact between the light blocking films 38C and the second transparent linear electrodes 38B, an insulator is disposed between the both. At the radiographic image detector 20 of the exemplary embodiment, the insulating layer 38D which is formed from SiO2 or the like is provided, as the insulator, between the reading photoconductive layer 32 and the substrate 40. A thickness of the insulating layer 38D may be about 0.01 to 10 μm. When forming the light blocking films 38C, given that the irradiation intensity of the reading light onto the first transparent linear electrodes 38A is Ub and the irradiation intensity onto the second transparent linear electrodes 38B is Uc, the light blocking films 38C may be made to be a thickness such that Ub/Uc≧5 is satisfied. The constant in the right side of the above formula is preferably made to be 8, and even more preferably made to be 12.

Further, given that the interval between the first transparent linear electrode 38A and the second transparent linear electrode 38B is Wbc, a width Wd of the light blocking film 38C may be made so as to satisfy:

$$Wc \leq Wd \leq (Wc+2\times Wbc)$$

This conditional formula indicates that the light blocking films 38C completely cover at least the second transparent linear electrodes 38B, and the light blocking films 38C do not span to the portions corresponding to the first transparent linear electrodes 38A so that at least portions corresponding to the widths Wb of the first transparent linear electrodes 38A are ensured as transmitting portions of the reading light. However, if the light blocking films 38C are provided only at portions corresponding to the widths Wc of the second transparent linear electrodes 38B, the light blocking may be insufficient, and if the transmitting portions of the reading light are only portions corresponding to the widths Wb of the first transparent linear electrodes 38A, there is the concern that the reading light which reaches the first transparent linear electrodes 38A may be insufficient. Therefore, it is more preferable to satisfy:

$$(Wc+Wbc/2) \leq Wd \leq (Wc+Wbc)$$

The above described radiographic image detector 20 corresponds to the radiographic image detector according to the present invention.

Further, as shown in FIG. 2, the radiation generator 12 and the radiation detector 14 are respectively connected to a controller 50. The controller 50 is structured to include a computer having a CPU, a memory formed from a RAM or the like, and a nonvolatile storage section 50A formed from an HDD (Hard Disk Drive) or the like (portions other than the storage section 50A are omitted from the drawing), and peripheral circuits which are connected to the computer. Due to predetermined programs which are stored in the nonvolatile storage section 50A being executed by the CPU of the computer and the computer and the peripheral circuits working in cooperation, the controller 50 functions as a radiation generation controller 66 which controls the generation of radiation at the radiation generator 12, and functions as an image read-out section 68 which reads out of image information from the radiographic image detector 20. A display 52 for displaying radiographic images is also connected to the controller 50.

As shown in FIG. 4, the image read-out section 68 is structured to include the aforementioned linear light source 54. The linear light source 54 is structured such that a large number of LEDs (e.g., LEDs which emit B light), are arrayed along the direction (the main scanning direction) in which the second transparent linear electrodes 38B (and the first transparent linear electrodes 38A) are arrayed at the radiographic image detector 20. At the time of reading-out image information from the radiographic image detector 20, the large number of LEDs are respectively lit by a driving circuit (not shown) which is a part of the image read-out section 68, and irradiate reading light which is linear onto the substrate 40 side surface of the radiographic image detector 20. The linear light source 54 is supported so as to be movable above the substrate 40 side surface of the radiographic image detector 20 along the direction in which the second transparent linear electrodes 38B extend (the subscanning direction (read-out direction): the direction of arrow A in FIG. 4), by an unillustrated moving mechanism which is a part of the image read-out section 68. At the time of reading-out image information from the radiographic image detector 20, the linear light source 54 is moved (subscanned) in the subscanning direction at a uniform moving speed by the moving mechanism. In this way, the linear reading light is irradiated in order onto the entire substrate 40 side surface of the radiographic image detector 20.

The image read-out section 68 includes plural charge amplifiers 56, a high-voltage power source 58, a multiplexer (MPX) 60, and an A/D converter 62. The respective charge amplifiers 56 are connected to respectively different second transparent linear electrodes 38B of the radiographic image detector 20. The high-voltage power source 58 applies high voltage between the substrate 40 and the individual second transparent linear electrodes 38B via the charge amplifiers 56, when radiation is irradiated onto the radiographic image detector 20. The multiplexer 60 is connected to the respective output terminals of the plural charge amplifiers 56, and selectively outputs an electrical signal which is inputted from any of the charge amplifiers 56. The A/D converter 62 is connected to the output terminal of the multiplexer 60, and converts the electrical signal inputted via the multiplexer 60 into digital data, and outputs the digital data.

At the radiographic image detector 20, when the linear reading light emitted from the linear light source 54 is irradiated, among the image information recorded in the radiographic image detector 20, which is formed by latent image polarity charges accumulated in the charge accumulating section 30, the image information of one line which is recorded at the portion where the reading light is irradiated is, via the individual second transparent linear electrodes 38B, outputted, for each unit region, as electrical signals of levels corresponding to the amounts of the latent image polarity charges for the respective pixels. The multiplexer 60 switches, in order, the electrical signals outputted to the A/D converter 62 so that the electrical signals, which are outputted via the individual second transparent linear electrodes 38B and are amplified by the charge amplifiers 56, are outputted in order (sequentially) to the A/D converter 62. In this way, image data of one line is outputted in order from the A/D converter 62. By repeating the above-described processings during the time until the linear reading light emitted from the linear light source 54 is irradiated onto the entire substrate 40 side surface of the radiographic image detector 20, all of the image information of the surface of the image recorded in the radiographic image detector 20 is read-out as image data.

Further, an image processing program also is stored in the storage section 50A of the controller 50. Due to this image processing program being executed by the CPU, the controller 50 functions also as an image processor 70 shown in FIG. 4. The image processor 70, which is realized by this image processing program being executed, corresponds to the image processing device relating to the present invention. The image processing program includes a leakage current correction program to perform correction to the leakage current as described below. This leakage current correction program corresponds to the image processing program relating to the present invention.

Figure 5A:
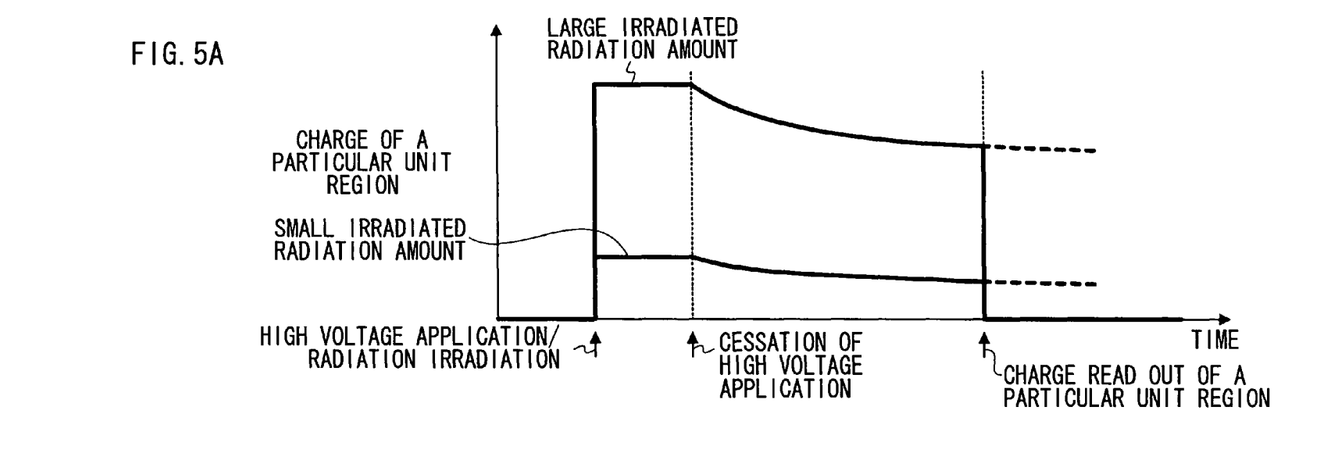
FIG. 5A is a graph showing a charge of a particular unit region.

Explanation will now be given of the operation of the exemplary embodiment. FIG. 5A shows the transition of charge (latent image polarity charge) accumulated/held in individual unit regions of the radiographic image detector 20. As shown in FIG. 5A, the charge in the individual unit regions of the radiographic image detector 20 is initially zero. However, when radiation carrying image information is irradiated in a state in which a high voltage is applied by the high-voltage power source 58 to the radiographic image detector 20, charges are generated in the recording photoconductive layer 28 with charge amounts that correspond to the amount of irradiated radiation, and the generated charges are accumulated/held in the individual unit regions. When the high voltage applied by the high-voltage power source 58 ceases to be applied in order to read out the image from the radiographic image detector 20, it is apparent from the results of investigations undertaken by the inventors that leakage current occurs and gradually attenuates with time (see FIG. 5B).

Figure 5B:
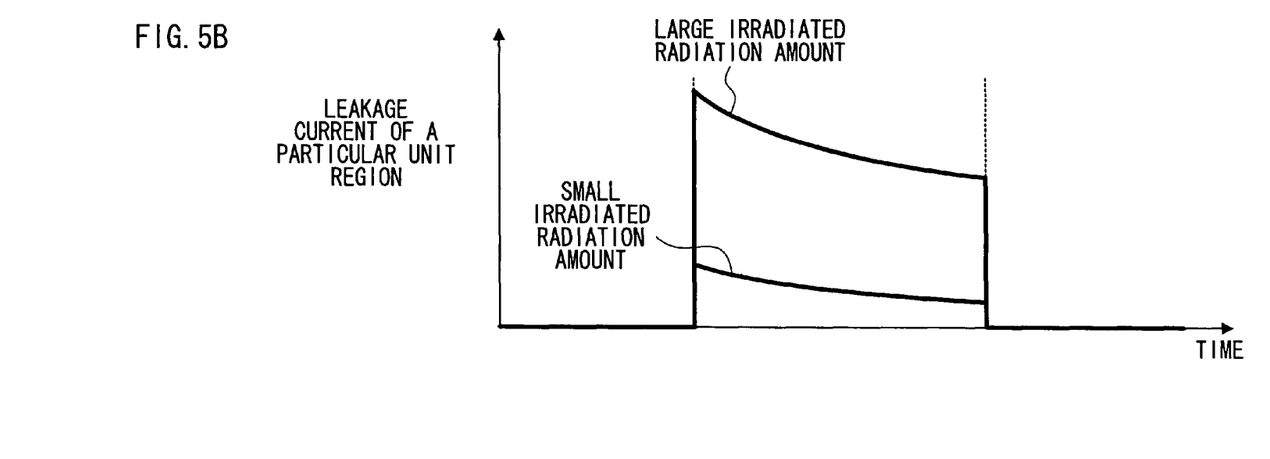
FIG. 5B is a graph showing transition of the leakage current in the particular unit region.

This leakage current is superimposed on read-out current when charge is read out from other unit regions. As the leakage current is generated, the charge accumulated/held in the individual unit regions also gradually decreases. Then, when the charge is read out from a particular unit region as read out of the image progresses, the charge of the particular unit region becomes zero, and the leakage current of the particular unit region also becomes zero.

Figure 6:
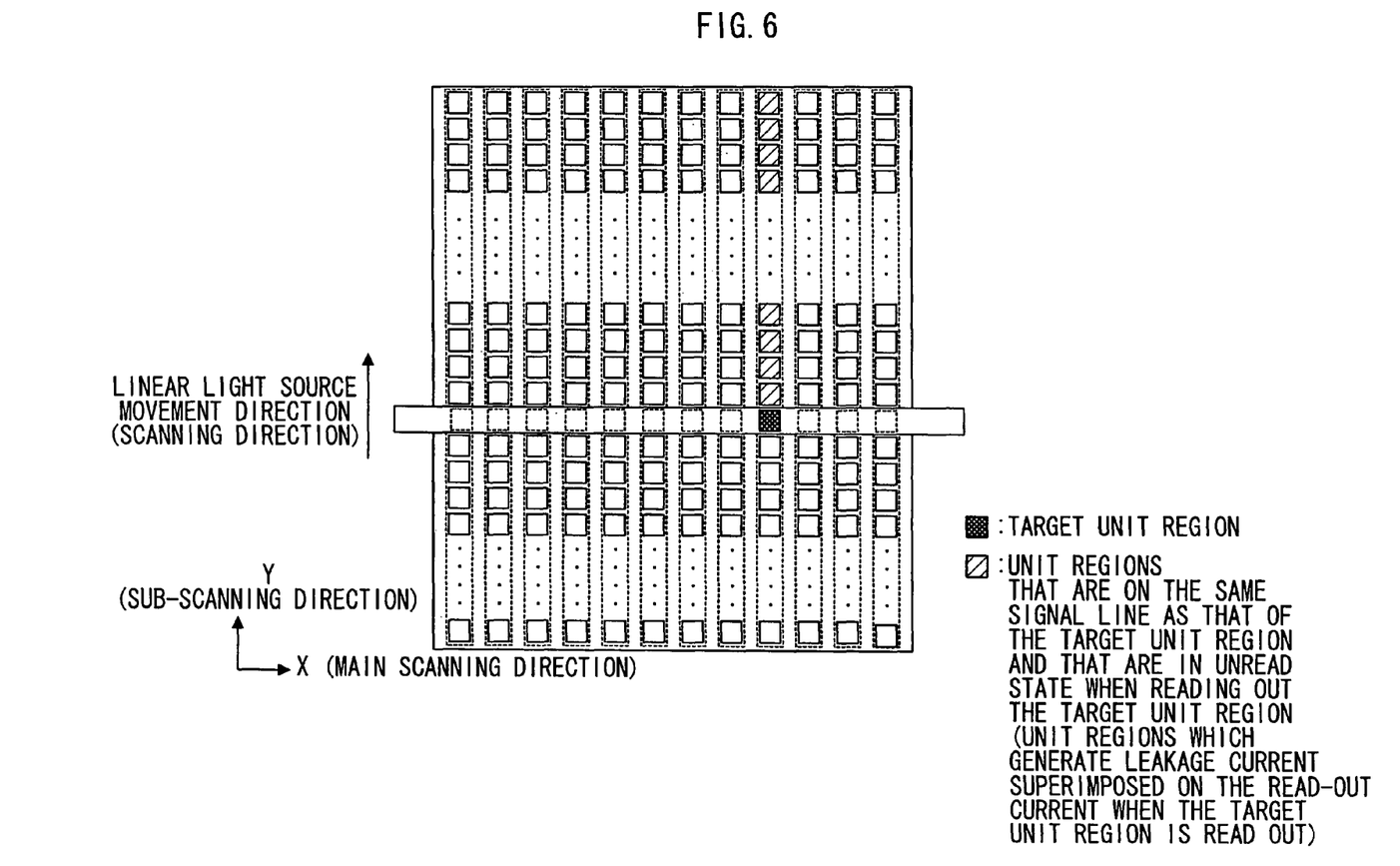
FIG. 6 is a schematic diagram showing a target unit region and the influence from the leakage current of each of the unit regions during charge read-out for the target unit region.

As described above, the duration of leakage current generation in the individual unit regions of the radiographic image detector 20 is the period from when application of the high voltage ceases up to the time when the charge accumulated/held in the individual unit regions is read out. The leakage current generated in the individual unit regions is superimposed on the read-out current flowing in the second transparent linear electrode 38B, corresponding to the respective unit region of the second transparent linear electrodes 38B provided in the radiographic image detector 20. Therefore, as shown in FIG. 6, when the charge of a particular unit region under consideration (shown in FIG. 6 as the "target unit region") is read out through the second transparent linear electrode 38B, the read-out current is superimposed with leakage current from the unit regions (unit regions shown by hatching in FIG. 6) that are positioned on the same signal line along the linear light source 54 movement direction (sub-scanning direction) as the particular unit region (i.e., correspond to the same second transparent linear electrode 38B as that of the particular unit region), and that are also in an unread state when the charge of the particular unit region is being read out. It should be noted that while individual unit regions are shown in FIG. 6 as box shapes, this is simply a representation of the positions of the individual unit regions, and the charge read-out regions of charge accumulated/held in the individual unit regions may not exactly match the ranges of the box shape regions shown.

When image data read out from the radiographic image detector 20 by the image read-out section 68 is input to the image processor 70, after carrying out the leakage current correction processing (described below) on the input image data, a radiographic image representing the image data can be displayed on the display 52 by outputting to the display 52 image data to which the leakage current correction processed is performed. Explanation will now be given of the leakage current correction processing with reference to FIG. 7. It should be noted that the leakage current correction processing is processing which the image processing (correction) method according to the present invention is applied, and corresponds to the correction section of the present invention.

Figure 7:
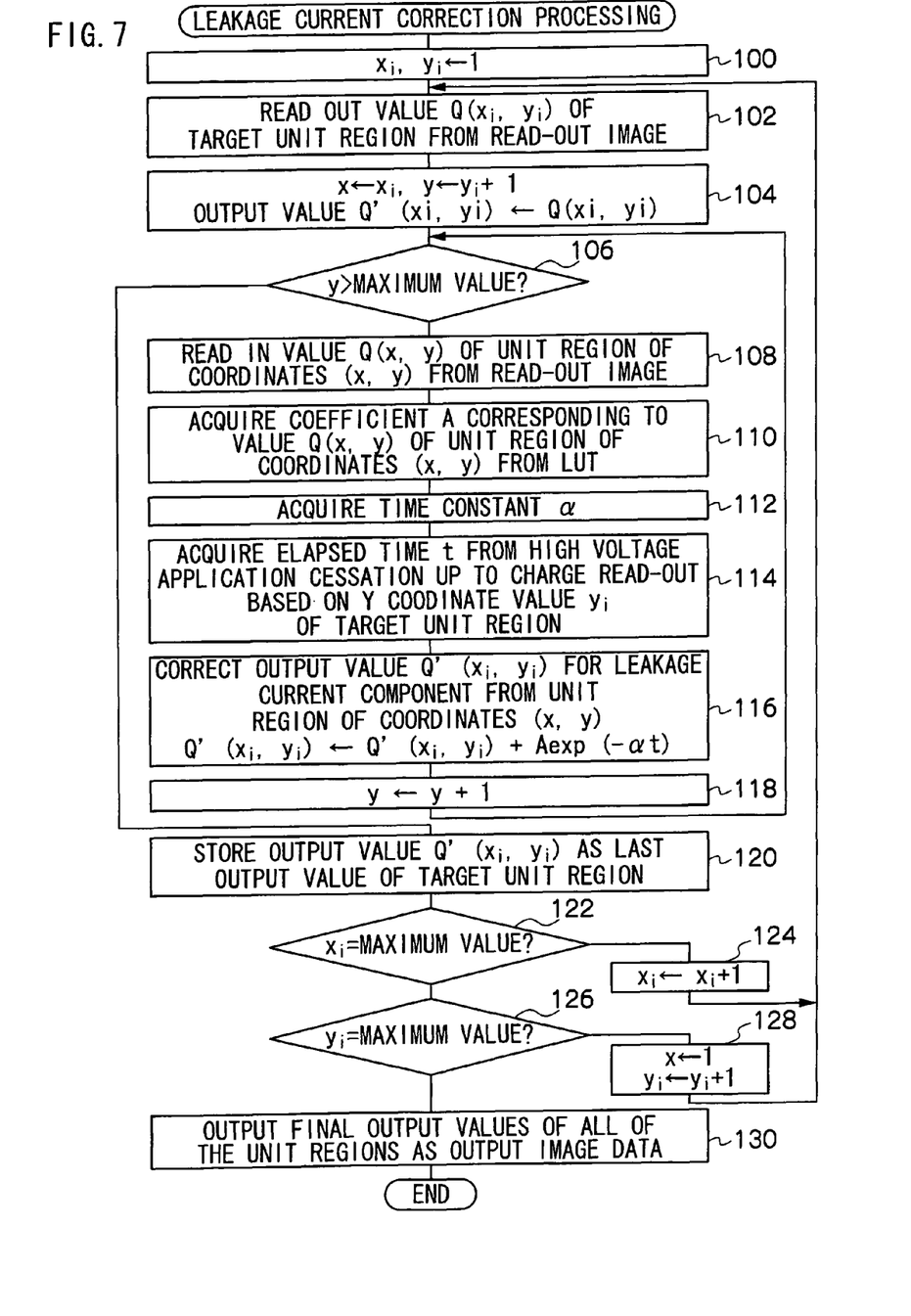
FIG. 7 is a flow chart showing the contents of leakage current correction processing.

In the leakage current correction processing, at step 100, the variable $x_i$ and the variable $y_i$, representing the position (coordinates) of the unit region to be target of the leakage current correction in the radiographic image detector 20, are both substituted with 1. In the exemplary embodiment, the variable x represents the position (X coordinate value) in the main scanning direction, and the variable y represents the position (Y coordinate value) in the sub-scanning direction (see FIG. 6). Next, at step 102, the value $Q(x_i, y_i)$ of the target unit region are read in from the read-out image (input image data). At step 104, the variable $x_i$ is set as the variable x representing the position (X coordinate value) of the reference unit region, and the variable $y_i$ plus 1 is set as the value of the variable y representing the position (Y coordinate value) of the reference unit region. In such a case, the first unit region downstream in the sub-scanning direction from the target unit region is specified as a reference unit region by the variables x, y. The value $Q(x_i, y_i)$ of the target unit region read-in at step 102 are set as the output value $Q'(x_i, y_i)$ of the target unit region. Next, at step 106, determination is made as to whether or not the value of variable y is greater than the maximum value (total number of unit regions of the radiographic image detector 20 along the sub-scanning direction). When determination is negative, the routine proceeds to step 108, and the value Q(x, y) of the unit region of coordinates (x, y), namely the reference unit region, are read in from the read-out image (input image data).

In the exemplary embodiment, the leakage current correction data, for use in the leakage current correction processing, is stored in advance in the storage section 50A of the controller 50. In the exemplary embodiment, by updating the output value $Q'(x_i, y_i)$ of the target unit region according to the following Formula (1), correction is made for the influence of leakage current in the reference unit region superimposed on the read-out current.

$$Q'(x_i,y_i) \leftarrow Q'(x_i,y_i) + A\exp(-\alpha t) \quad (1)$$

In Formula (1): t is the duration from when the high voltage ceases to be applied to the radiographic image detector 20 up to the time of read out of charge of the target unit region; A is a coefficient depending on the amount of charge read out from the reference unit region (i.e., the value Q(x, y) of the reference unit region); and $\alpha$ is a time constant. The second term on the right side of Formula 1 represents the leakage current, and corresponds to the leakage current estimation equation according to the present invention. Also, as shown in FIG. 1, the leakage current in the exemplary embodiment is a current of the opposite direction to the read-out current (the read-out current is reduced by the leakage current component), therefore for the leakage current estimation equation, the second term on the right side of Formula (1) is added to the first term thereof. However, if the leakage current occurs in the same direction as the read-out current, a leakage current estimation equation in which the second term on the right side of Formula (1) is subtracted from the first term on the right side thereof can be adopted. In the leakage current correction data, there is a LUT (Look Up Table) in which the above Formula (1), the time constant $\alpha$, and values of coefficient A for each value taken for the values of Q(x, y) of the reference unit region are stored in relation with each other.

As seen from comparison of the leakage current for a case of "Irradiated Radiation Amount: Large" of FIG. 5B with that of a case of "Irradiated Radiation Amount: Small", the size of the leakage current in the individual unit regions of the radiographic image detector 20 are different depending on the amount of irradiated radiation onto the individual unit regions, namely, different depending on the charge amount of the individual unit regions. The coefficient A is a coefficient for varying the size of the leakage current in the reference unit region represented by the second term on the right side of Formula (1) according to the charge amount of the reference unit region (value Q(x, y) of the reference unit region). Data set in the above LUT, may be obtained, for example as in the investigations carried out by the inventor, by measuring the respective variation patterns of the leakage current (sum thereof) for each value of irradiated radiation amount, and deriving the relationship between the irradiated radiation amount (charge amount of the reference unit region=value Q(x, y) of the reference unit region) and the size of the leakage current in the reference unit region. Moreover, although a uniform value is used for the time constant $\alpha$ in the exemplary embodiment, when, as a result of performing the above measurements, it is found that the attenuation speed of the leakage current varies greatly in relation with the irradiated radiation amount (i.e., when there is a strong correlation therebetween), similarly to the coefficient A, the time constant $\alpha$ may be also varied according to the charge amount of the reference unit region.

At step 110, the LUT for setting the value of coefficient A is read out from the leakage current correction data in the storage section 50A of the controller 50 and stored in the memory, and the value of the coefficient A corresponding to the value Q(x,y) of the reference unit region stored in the memory is acquired. At step 112, the value of the time constant $\alpha$ is read out from the leakage current correction data in storage section 50A. At step 114, the elapsed time t from the cessation of application of high voltage to the radiographic image detector 20 up to the charge read out from the target unit region is acquired, based on the y coordinate value $y_i$ of the target unit region. It should be noted that usually the time t1, from cessation of application of high voltage to the radiographic image detector 20 up to reading out the image (charge) from the radiographic image detector 20, and the time t2, which is the time required for reading out the charge from the radiographic image detector 20 for one line's worth of unit region in the main scanning direction, are constant. Therefore, the above elapsed time t may be acquired, for example, by storing the times t1, t2 in the leakage current correction data, reading out t1, t2 from the storage section 50A in step 114, and computing the elapsed time t by adding to time t1 the product of a value $y_i$, which is Y coordinate value of the target unit region, and time t2.

Then, at step 116, Formula (1) is read out from the leakage current correction data in the storage section 50A, and the output value $Q'(x_i, y_i)$ of the target unit region current, the coefficient A acquired in step 110, the time constant $\alpha$ read out in step 112, and the elapsed time t acquired in step 114, are each substituted in Formula (1), and the new output value $Q'(x_i, y_i)$ is computed. Thereby, the output value $Q'(x_i, y_i)$ for the target unit region is corrected according to the leakage current in the reference unit region that was superimposed on the read-out current when the charge was read out from the target unit region, and the influence of the leakage current of the reference unit region is removed from the output value $Q'(x_i, y_i)$ of the target unit region.

It should be noted that the second term on the right side of the Formula (1), corresponding to the leakage current estimation equation, may use an elapsed time t from the time of starting reading out the charge of the radiographic image detector 20 up to the time when the charge is read out from the target unit region (the time equivalent to the product of the Y coordinate value $y_i$ of the target unit region and the time t2), in place of the elapsed time t from the cessation of application of high voltage to the radiographic image detector 20 up to the time when the charge being read out from the target unit region. In such a case, the same values as in Formula (1) may be used for the coefficient A and time constant $\alpha$, as long as the time t1 is a sufficiently small value. Even if the value of time t1 is too large to be ignored, the leakage current may be similarly estimated with high precision with Formula (1) by determining different values of coefficient A and time constant $\alpha$ corresponding to the time t1.

Next, at step 118, variable y is incremented by 1 and the routine returns to step 106. Step 106 to step 118 are thereby repeated until the determination at step 106 become affirmative. Namely, the processing of step 106 to step 118 is repeated for all of the unit regions (the unit regions shown by hatching in FIG. 6) that are positioned on the same signal line along the linear light source 54 movement direction as the target unit region (unit regions having the same X coordinate as that of the target unit region) and that are in an unread state when the charge of the target unit region is being read out (unit regions having a Y coordinate that is larger than that of the target unit region). The influence of leakage currents, in the individual unit regions are thereby all removed from the output value $Q'(x_i, y_i)$ of the target unit region.

When the influence of leakage currents in each of the individual unit regions are all removed from the output value $Q'(x_i, y_i)$ of the target unit region and the determination at step 106 is affirmative, the routine proceeds to step 120, and the output value $Q'(x_i, y_i)$ is stored in the memory as the final output value for the target unit region. Next, at step 122, determination is made as to whether the current variable $x_i$ matches the maximum value (the total number of the unit regions of the radiographic image detector 20 in the main scanning direction). When determination is negative, the routine proceeds to step 124, the variable $x_i$ is incremented by 1, and then the routine returns to step 102. The adjacent unit region downstream in the main scanning direction with respect to the previous target unit region is thereby set as the new target unit region, the processing of step 106 to step 118 is repeated, and the output value $Q'(x_i, y_i)$ corrected for the influence of leakage current is computed. Since the processing of step 102 to step 124 is repeated until the determination at step 122 becomes affirmative, the final output values corrected for the influence of leakage current are computed for each of the unit regions on the same main scanning line.

When determination at step 122 is affirmative, the routine proceeds to step 126, and determination is made as to whether the current variable $y_i$ matches the maximum value (the total number of the unit regions of the radiographic image detector 20 in the sub-scanning direction). If determination is negative, the routine proceeds to step 128, and the variable $x_i$ is set to 1 and the variable $y_i$ is incremented by 1, then the routine returns to step 102. The unit region at the head of the main scanning line positioned downstream in the sub-scanning direction with respect to the previous target unit region is thereby set as the new target unit region, and the processing of step 102 to step 118 is repeated. Since processing of step 102 to step 128 is repeated until the determination at step 126 becomes affirmative, the final output values which is corrected for the influence of leakage current are computed sequentially for all of the unit regions in the radiographic image detector 20. Then, when the final output values which is corrected for the influence of leakage current have been computed for all of the unit regions of the radiographic image detector 20, the determination at step 126 will be affirmative, the routine proceeds to step 130, the final output values for all of the unit regions are output as output image data, and the leakage current correction processing is complete.

By this processing, output image data which is corrected with good precision for the influence of leakage current superimposed on the read-out current from the radiographic image detector 20 can be obtained. A high quality radiographic image may be displayed on the display 52 by using this output image data for displaying an image on the display 52. Instead of displaying the image on the display 52, processing may be carried out, such as storing the image data on a flash memory or other information storage medium, or recording the image on a sheet recording material using a printer or the like.

The leakage current correction processing shown in FIG. 7 uses an algorithm for removing the influence of leakage current in each of the unit regions from the output value $Q'(x_i, y_i)$ of the target unit region, by correcting the output value $Q'(x_i, y_i)$ for target unit regions according to the leakage current in a particular reference unit region using Formula (1), and repeating this correction for the target unit region with reference unit regions of each unit region that is positioned on the same signal line along the linear light source 54 movement direction (unit regions having the same X coordinate as that of the target unit region) and whose charges are in an unread state when the charge of the target unit region is being read out (unit regions having a Y coordinate that is larger than that of the target unit region). However, the embodiment is not limited thereto, and an algorithm for removing the influence of leakage current in each of the unit regions from the output value $Q'(x_i, y_i)$ of the target unit region, by sequentially computing the leakage currents of each of the unit regions according to the second term on the right side of Formula (1), and thereafter, adding (or subtracting) an integrated value or cumulative value of the computed leakage current in each the unit regions to/from the output value $Q'(x_i, y_i)$ may be used.

The leakage current estimation equation (the second term on the right side of Formula (1)) used in the exemplary embodiment is formed from an exponential function in which the elapsed time t from cessation of application of high voltage to the radiographic image detector 20 (the time when leakage current is generated in the unit region) up to the time when the charge is read out from the target unit region (or the elapsed time t from starting to read out the charge of the radiographic image detector 20 up to the charge read-out from the target unit region) as a variable. However, the present invention is not limited thereto, and since the time t2, which is required for reading out the charge of one line's worth of unit regions in the main scanning direction from the radiographic image detector 20, is constant, a leakage current estimation equation may be used which is formed from an exponential function with the position y of the target unit region in the movement direction of the linear light source 54 (sub-scanning direction) as a variable in place of the above described elapsed time. This position y may be the Y coordinate value $y_i$ of the target unit region, or may be the distance along the sub-scanning direction from the start position of movement of the linear light source 54 up to the position of the target unit region, computed from the coordinate value $y_i$. Also in this case, the leakage current may be estimated with high precision, similarly as in the leakage current estimation equation formed from the exponential function with elapsed time t as a variable.

Figure 8:
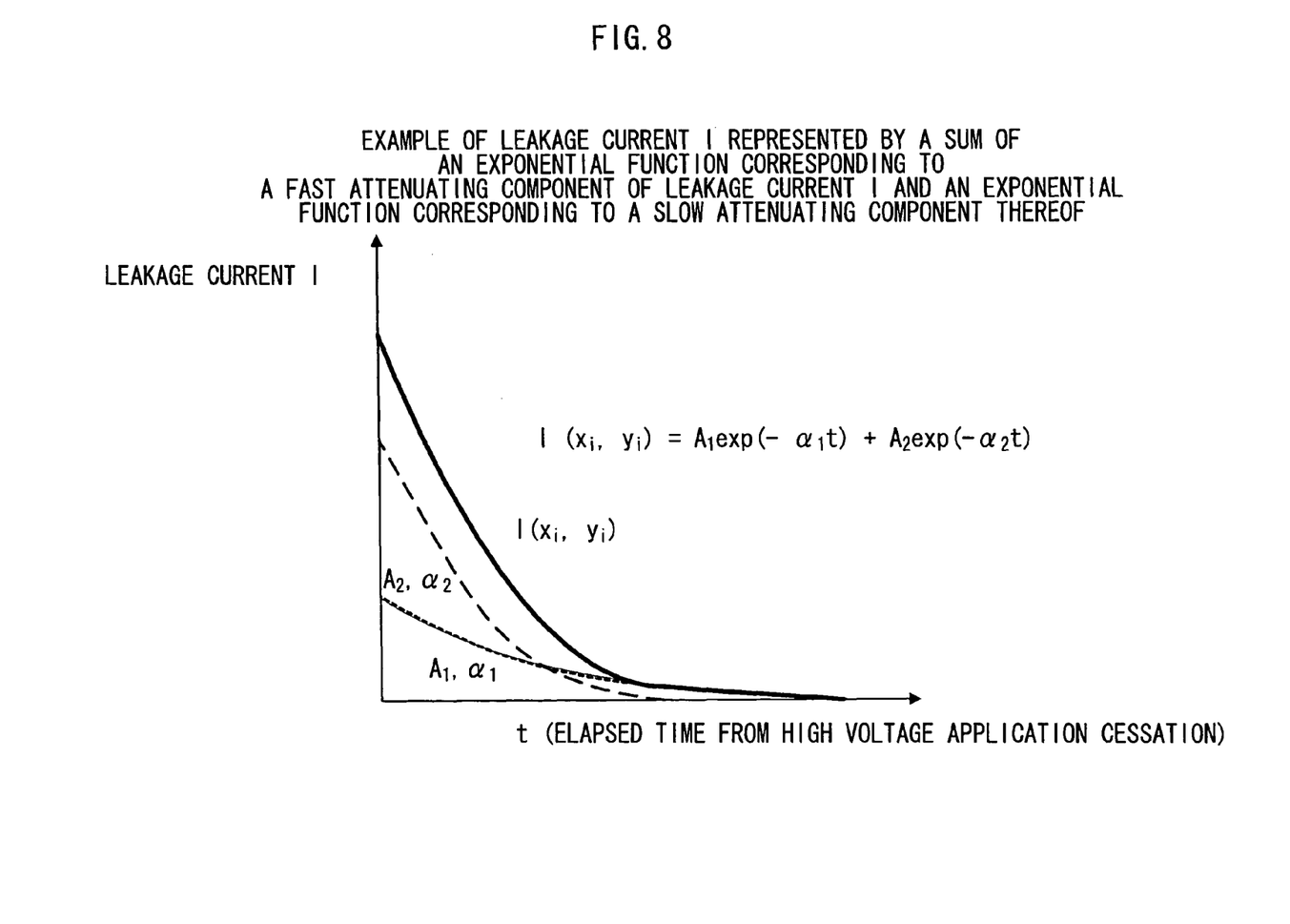
FIG. 8 is a graph showing an example of leakage current transition as the sum of an exponential function corresponding to a component with fast attenuation and an exponential function corresponding to a component with slow attenuation.

Further, the leakage current estimation equation (the second term on the right hand side of Formula (1)) used in the exemplary embodiment is formed from a single exponential function, in which the elapsed time t from cessation of application of high voltage to the radiographic image detector 20 (the time when leakage current is generated in the unit region) up to the charge read out from the target unit region (or the elapsed time t from starting to read out the charge of the radiographic image detector 20 up to the charge read out from the target unit region) as a variable. However, the present invention is not limited thereto. The leakage current change transition (change pattern) varies depending on the configuration of the radiographic image detector 20 (for example, depending on the materials of each component and the like). Therefore, for example, when the sum of plural exponential functions (for example an exponential function corresponding to a component with fast attenuation and an exponential function corresponding to a component with slow attenuation, as shown in FIG. 8) provides a more precise approximation of the leakage current change transition (change pattern), a leakage current estimation equation formed from the sum of plural exponential functions may be used. Such exponential functions may be exponential functions with the elapsed time t as a variable, or may be exponential functions with the position y of the target unit region in the sub-scanning direction as a variable.

Furthermore, in the exemplary embodiment, correction is carried out to the output value $Q'(x_i, y_i)$ of the target unit region for the leakage current from the unit regions that are the source of leakage current generation when reading out the charge from the target unit region (i.e., the unit regions that are positioned on the same signal line along the linear light source 54 movement direction (sub-scanning direction) as the target unit region and whose charges are in an unread state when the charge of the target unit region is being read out). However, as seen from FIG. 5A, the charge amount of the individual unit regions gradually reduces due to the current leakage therefrom. Accordingly, when correcting the output value $Q'(x_i, y_i)$ of the target unit region, based on the fact that the charge amount of the target unit region when the charge is being read out from the target unit region is reduced from initial charge amount by an amount according to the elapsed time t from cessation of application of high voltage to the radiographic image detector 20, the charge reduction amount of the target unit region that accompanies the current leakage from the target unit region may be estimated based on the elapsed time t, and the output value $Q'(x_i, y_i)$ may be increased by the estimated charge reduction amount.

Moreover, explanation has been given using an example of an optical reading-type radiographic image detector 20 as the radiographic image detector used in the exemplary embodiment. However, the present invention is not limited thereto. For example, another type of radiographic image detector, such as a TFT type may be used. Also in this type of radiographic image detector, since the electrical resistance for holding the charge of the individual unit regions is not infinite, leakage current is generated from each of the unit regions, and the size of the leakage current gradually reduces with the passage of time. Accordingly, also in this type of radiographic image detector, correction with high precision may be made for the influence of leakage current by using the leakage current correction of the exemplary embodiment.

Furthermore, explanation was given that the image processing program according to the present invention is stored (installed) in advance in the storage section 50A of the controller 50. However, the present invention is not limited thereto, and the image processing program may also be provided by stored on a storage medium such as a CD-ROM, DVD-ROM or the like.

As described above, the image processing device of the exemplary embodiment is directed to process image data obtained by sequentially reading out the charge, as a current, from each of unit regions to be read out from the radiographic image detector, through signal lines provided along a predetermined direction in the radiographic image detector. An optical reading-type radiographic image detector may be used as the above radiographic image detector, or another configuration, such as a TFT type, may also be applied as the radiographic image detector.

The correction section of the image processing device estimates the respective leakage current superimposed on the read-out current when the charge is read out from a target unit region using a leakage current estimation equation, formed from a single exponential function or from a sum of plural exponential functions. The exponential function(s) may estimate respective leakage currents $I_j$ of unit regions j (j=1, 2, . . . ) that are positioned along the predetermined direction on the same signal line as that of the target unit region and that are in an unread state when the charge is being read out from the target unit region. The exponential function(s) may have as a variable one of (a) elapsed time from the time of leakage current generation of the unit region j up to the time when charge is read out therefrom, (b) elapsed time from starting to read out charge of the radiographic image detector up to the time when charge is read out from the unit region j, or (c) position of the unit region j along the predetermined direction of the target unit region when charge is read out therefrom by scanning the charge read-out target unit regions along the predetermined direction.

The unit region j (j=1, 2, . . . ) is a unit region from which a leakage current $I_j$ is generated and superimposed on the read-out current when charge is read out from the target unit region from the radiographic image detector. The correction section estimates the respective leakage currents $I_j$ in the unit regions j (j=1, 2, . . . ) using a leakage current estimation equation formed from a single exponential function or plural exponential functions having a variable of any one of above described (a), (b) or (c). Accordingly, the change due to attenuation with time of the leakage current is considered in the estimation, and the leakage current $I_j$ from the unit regions j (j=1, 2, . . . ) may be estimated with high precision.

The correction section corrects data corresponding to the target unit region in the image data based on the results of the above described leakage current estimation. The data corresponding to the target unit region may thereby be corrected with high precision so as to remove the influence of the leakage current superimposed on the read-out current when the charge is read out from the target unit region. Further, for each of the individual unit regions as the target unit region, the correction section estimates the leakage current of the unit regions j (j=1, 2, . . . ) as described above, and corrects the data corresponding to the target unit region from the image data, based on the respective leakage current estimate result. Correction may accordingly be made with high precision for each of the individual unit regions in the whole image data so as to remove from the charge the influence of leakage current superimposed on the read-out current. Therefore, high precision correction for the influence of leakage current superimposed on the read-out current from the radiographic image detector with respect to the whole image data which is read out from the radiographic image detector is enabled by the image processing device.

The correction section may estimate the respective leakage currents $I_j$ for the unit regions j (j=1, 2, . . . ) using the leakage current estimation equation formed from the following single exponential function including the variable (a) or the variable (b), $$I_j = A_j \cdot \exp(-\alpha t)$$

wherein: t is the elapsed time from the time of leakage current generation of the unit region j, or is the elapsed time from starting to read out charge of the radiographic image detector; $A_j$ is a coefficient substantially dependent on the charge amount of the unit region j; and $\alpha$ is a constant.

The correction section may estimate the respective leakage currents $I_j$ for the unit regions j (j=1, 2, . . . ) using the leakage current estimation equation formed from the following sum of a plurality of exponential functions including the variable (a) or the variable (b), $$I_j = \Sigma A_{jk} \cdot \exp(-\alpha k t)$$

wherein: t is the elapsed time from the time of leakage current generation of the unit region j, or is the elapsed time from starting to read out charge of the radiographic image detector; $A_{jk}$ is a $k^{th}$ coefficient substantially dependent on the charge amount of the unit region j; and $\alpha k$ is a $k^{th}$ constant.

The correction section may estimate the respective leakage currents $I_j$ for the unit regions j (j=1, 2, . . . ) using the leakage current estimation equation formed from the following single exponential function including the variable (c), $$I_j = A_j \cdot \exp(-\alpha y)$$

wherein: y is the position along the predetermined direction of the target unit region, when charge is read out therefrom by scanning the target unit regions to be readout along the predetermined direction; $A_j$ is a coefficient substantially dependent on the charge amount of the unit region j; and α is a constant.

The correction section may estimate the respective leakage currents $I_j$ for the unit regions j (j=1, 2, ... ) using the leakage current estimation equation formed from the following sum of a plurality of exponential functions including the variable (c), $$I_j = \Sigma A_{jk} \cdot \exp(-\alpha k y)$$

wherein: y is the position along the predetermined direction of the target unit region when charge is read out therefrom by scanning the target unit regions to be readout along the predetermined direction; $A_{jk}$ is a $k^{th}$ coefficient substantially dependent on the charge amount of the unit region j; and αk is a $k^{th}$ constant.

After the correction section estimates the respective leakage currents $I_j$ for the unit regions j (j=1, 2, ... ), the total leakage current I superimposed on the read-out current when the charge is read out from the target unit region may be derived by integrating or cumulating the leakage current $I_j$ of the unit regions j (j=1, 2, ... ), and the data corresponding to the target unit region from the image data is corrected on the basis of the total leakage current I.

The radiographic image detector may be provided with, as the signal lines, a plurality of read-out electrodes arrayed in a direction intersecting with the predetermined direction, and the radiographic image detector may be configured such that due to irradiation of radiation, the charge corresponding to the charge amount held in the unit region of the location irradiated with radiation, is output as a current through the corresponding read-out electrode; and the read out of the charge held in the radiographic image detector may be performed by scanning the locations of radiation irradiation on the radiographic image detector along the predetermined direction.

Due to the configurations described above, high precision of correction for the influence of leakage current superimposed on read-out current from a radiographic image detector is enabled.

What is claimed is:

1. An image processing device processing image data obtained from a radiographic image detector that is provided with signal lines extending along a predetermined direction, converts irradiated radiation into charge, and accumulates and holds the converted charge, the image data being obtained by sequentially reading out, as a current through the signal lines, the charge from each of unit regions to be read out from the radiographic image detector, the device comprising:

a correction section that corrects the image data for each unit region, the correction section estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, ... ) that are positioned along the predetermined direction on the same signal line as that of the target unit region and whose charges are in an unread state when the charge of the target unit region is being read out, and the correction section correcting the image data corresponding to the target unit region on the basis of the leakage current estimate result;

wherein the exponential function(s) has as a variable one of:

(a) elapsed time from the time of leakage current generation of the unit region j up to when charge is read out therefrom, (b) elapsed time from starting to read out charge of the radiographic image detector up to when charge is read out from the unit region j, or (c) position along the predetermined direction of the target unit region when charge is read out therefrom by scanning the target unit regions to be readout along the predetermined direction.

2. The image processing device according to claim 1, wherein the correction section estimates the respective leakage currents $I_j$ for the unit regions j (j=1, 2, ... ) using the leakage current estimation equation formed from the following single exponential function including the variable (a) or the variable (b), $$I_j = A_j \cdot \exp(-at)$$

wherein: t is the elapsed time from the time of leakage current generation of the unit region j, or is the elapsed time from starting to read out charge of the radiographic image detector; $A_j$ is a coefficient substantially dependent on the charge amount of the unit region j; and α is a constant.

3. The image processing device according to claim 1, wherein the correction section estimates the respective leakage currents $I_j$ for the unit regions j (j=1, 2, ... ) using the leakage current estimation equation formed from the following sum of a plurality of exponential functions including the variable (a) or the variable (b), $$I_j = \Sigma A_{jk} \cdot \exp(-\alpha k t)$$

wherein: t is the elapsed time from the time of leakage current generation of the unit region j, or is the elapsed time from starting to read out charge of the radiographic image detector; $A_{jk}$ is a $k^{th}$ coefficient substantially dependent on the charge amount of the unit region j; and αk is a $k^{th}$ constant.

4. The image processing device according to claim 1, wherein the correction section estimates the respective leakage currents $I_j$ for the unit regions j (j=1, 2, ... ) using the leakage current estimation equation formed from the following single exponential function including the variable (c), $$I_j = A_j \cdot \exp(-\alpha y)$$

wherein: y is the position along the predetermined direction of the target unit region, when charge is read out therefrom by scanning the target unit regions to be readout along the predetermined direction; $A_j$ is a coefficient substantially dependent on the charge amount of the unit region j; and α is a constant.

5. The image processing device according to claim 1, wherein the correction section estimates the respective leakage currents $I_j$ for the unit regions j (j=1, 2, ... ) using the leakage current estimation equation formed from the following sum of a plurality of exponential functions including the variable (c), $$I_j = \Sigma A_{jk} \cdot \exp(-\alpha k y)$$

wherein: y is the position along the predetermined direction of the target unit region when charge is read out therefrom by scanning the target unit regions to be readout along the predetermined direction; $A_{jk}$ is a $k^{th}$ coefficient substantially dependent on the charge amount of the unit region j; and $\alpha k$ is a $k^{th}$ constant.

6. The image processing device according to claim 1, wherein, after the correction section estimates the respective leakage currents $I_j$ for the unit regions j (j=1, 2, ... ), the total leakage current I superimposed on the read-out current when the charge is read out from the target unit region is derived by integrating or cumulating the leakage current $I_j$ of the unit regions j (j=1, 2, ... ), and the data corresponding to the target unit region from the image data is corrected on the basis of the total leakage current I.

7. The image processing device according to claim 1, wherein:
   the radiographic image detector is provided with, as the signal lines, a plurality of read-out electrodes arrayed in a direction intersecting with the predetermined direction, and the radiographic image detector is configured such that due to irradiation of radiation, the charge corresponding to the charge amount held in the unit region of the location irradiated with radiation, is output as a current through the corresponding read-out electrode; and
   the read out of the charge held in the radiographic image detector is performed by scanning the locations of radiation irradiation on the radiographic image detector along the predetermined direction.

8. An image processing method processing image data obtained from a radiographic image detector being provided with signal lines extending along a predetermined direction, converting irradiated radiation into the charge, and accumulating and holding the converted charge, the image data being obtained by sequentially reading out a charge, as a current through signal lines, from each of unit regions to be read out from the radiographic image detector, the method comprising:
   correcting the image data for each unit region by estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, ... ) that are positioned along the predetermined direction on the same signal line as that of the target unit region and whose charges are in an unread state when the charge of the target unit region is being read out, and correcting the image data corresponding to the target unit region on the basis of the leakage current estimate result;
   wherein the exponential function(s) has as a variable one of:
   (a) elapsed time from the time of leakage current generation of the unit region j up to when charge is read out therefrom,
   (b) elapsed time from starting to read out charge of the radiographic image detector up to when charge is read out from the unit region j, or
   (c) position along the predetermined direction of the target unit region when charge is read out therefrom by scanning the target unit regions to be readout along the predetermined direction.

9. A non-transitory storage medium storing a program for causing a computer to execute image data processing on image data obtained from a radiographic image detector being provided with signal lines extending along a predetermined direction, converting irradiated radiation into the charge, and accumulating and holding the converted charge, the image data being obtained by sequentially reading out a charge, as a current through signal lines, from each of unit regions to be read out from the radiographic image detector, the image data processing comprising:
   correcting the image data for each unit region by estimating the respective leakage current superimposed on the read-out current when the charge is read out from a target unit region using a leakage current estimation equation, formed from a single exponential function or from a sum of a plurality of exponential functions, for respective leakage currents $I_j$ of unit regions j (j=1, 2, ... ) that are positioned along the predetermined direction on the same signal line as that of the target unit region and whose charges are in an unread state when the charge of the target unit region is being read out; and correcting the image data corresponding to the target unit region on the basis of the leakage current estimate result;
   wherein the exponential function(s) has as a variable one of:
   (a) elapsed time from the time of leakage current generation of the unit region j up to when charge is read out therefrom,
   (b) elapsed time from starting to read out charge of the radiographic image detector up to when charge is read out from the unit region j, or
   (c) position along the predetermined direction of the target unit region when charge is read out therefrom by scanning the target unit regions to be readout along the predetermined direction.

* * * * *